United States Patent
Yang et al.

(10) Patent No.: US 10,486,095 B2
(45) Date of Patent: Nov. 26, 2019

(54) 3D DEODORIZING FILTER

(71) Applicant: 3AC., LTD., Seoul (KR)

(72) Inventors: Hee Tae Yang, Suwon-si (KR); Mi Ra Kwon, Ansan-si (KR); Na Ri Kim, Suwon-si (KR); Jeong Gon Ko, Seoul (KR); Ki Yeong Kim, Incheon (KR); Yun Hee Lee, Gwangmyeong-si (KR); Kwang Hyeok Lee, Pyeongtaek-si (KR); Jin Hoon Kim, Suwon-si (KR)

(73) Assignee: 3AC., LTD., Seoul (KR)

( * ) Notice: Subject to any disclaimer, the term of this patent is extended or adjusted under 35 U.S.C. 154(b) by 141 days.

(21) Appl. No.: 15/559,136

(22) PCT Filed: Mar. 13, 2017

(86) PCT No.: PCT/KR2017/002680
§ 371 (c)(1),
(2) Date: Sep. 18, 2017

(87) PCT Pub. No.: WO2017/160037
PCT Pub. Date: Sep. 21, 2017

(65) Prior Publication Data
US 2018/0169557 A1 Jun. 21, 2018

(30) Foreign Application Priority Data
Mar. 14, 2016 (KR) .................... 10-2016-0030229

(51) Int. Cl.
*B01D 53/04* (2006.01)
*B01D 46/00* (2006.01)
(Continued)

(52) U.S. Cl.
CPC .......... *B01D 46/0036* (2013.01); *A61L 9/014* (2013.01); *B01D 46/10* (2013.01);
(Continued)

(58) Field of Classification Search
CPC .... A61L 9/14; A61L 2209/14; A61L 2209/22; B01J 20/20; B01D 53/04; B01D 53/0407;
(Continued)

(56) References Cited

U.S. PATENT DOCUMENTS 3,411,273 A * 11/1968 Duncan .................. B01D 45/16
55/481
3,630,007 A * 12/1971 Neumann .............. B01D 46/30
96/129
(Continued)

FOREIGN PATENT DOCUMENTS

JP 2002-306587 A 10/2002
JP 2003-207177 A 7/2003
(Continued)

OTHER PUBLICATIONS

KIPO Office Action for Korean Patent Application No. 10-2016-0030229 dated Dec. 28, 2016.
(Continued)

*Primary Examiner* — Frank M Lawrence, Jr.
(74) *Attorney, Agent, or Firm* — Sughrue Mion, PLLC

(57) ABSTRACT

The present invention relates to a filter core for deodorizing agent filling and a deodorizing filter employing the same. More particularly, the present invention relates to a filter core for deodorizing agent filling and a deodorizing filter employing the same, in which an airflow path to be formed in multiple directions thus enhancing the airflow performance and improving the deodorizing efficiency. Accordingly, airflow can be generated in various directions so that airflow can efficiently flow and the pressure loss due to airflow can be reduced, thereby improving the deodorizing performance. In addition, the path through which the odor components are removed while air passes through the deodorizing agent is increased, thereby increasing a time
(Continued)

that air is in contact with the deodorizing agent and improving the deodorizing efficiency.

11 Claims, 8 Drawing Sheets

(51) Int. Cl.
*A61L 9/014* (2006.01)
*B01D 46/24* (2006.01)
*B01D 46/52* (2006.01)
*B01J 20/20* (2006.01)
*B01D 46/10* (2006.01)

(52) U.S. Cl.
CPC ......... *B01D 46/24* (2013.01); *B01D 46/2403* (2013.01); *B01D 46/521* (2013.01); *B01D 53/0407* (2013.01); *B01D 53/0415* (2013.01); *B01J 20/20* (2013.01); *A61L 2209/14* (2013.01); *A61L 2209/22* (2013.01); *B01D 46/0038* (2013.01); *B01D 2253/102* (2013.01); *B01D 2253/108* (2013.01); *B01D 2257/90* (2013.01); *B01D 2258/06* (2013.01)

(58) Field of Classification Search
CPC .......... B01D 53/0415; B01D 2253/102; B01D 2253/108; B01D 2257/90; B01D 2258/06
USPC .................... 96/134, 136, 147, 154; 422/120
See application file for complete search history.

(56) References Cited

U.S. PATENT DOCUMENTS

| | | | | |
|---|---|---|---|---|
| 3,675,394 A * | 7/1972 | Sterrett | .................. | B01D 46/30 55/515 |
| 4,917,862 A * | 4/1990 | Kraw | .................... | B01D 46/10 422/122 |
| 5,354,365 A * | 10/1994 | Youn | .................. | B01D 46/0036 55/487 |
| 5,750,026 A * | 5/1998 | Gadkaree | ........... | B01D 39/2003 210/502.1 |
| 8,202,350 B2 * | 6/2012 | Asaro | ................ | B01D 53/0407 95/148 |
| 2002/0139251 A1* | 10/2002 | Simmons | ........... | B01D 46/0036 96/134 |
| 2006/0101999 A1* | 5/2006 | Steins | ................ | B01D 46/0036 96/134 |
| 2014/0290492 A1* | 10/2014 | Lomax | ..................... | F15D 1/02 96/130 |

FOREIGN PATENT DOCUMENTS

| | | | |
|---|---|---|---|
| JP | 2006-288980 A | | 10/2006 |
| JP | 2008-113935 A | | 5/2008 |
| KR | 2006089845 | * | 2/2005 |
| KR | 10-0637702 B1 | | 10/2006 |
| KR | 10-2009-0035883 A | | 4/2009 |

OTHER PUBLICATIONS

International Search Report for PCT/KR2017/002680 dated Jun. 20, 2017 [PCT/ISA/210].

* cited by examiner

3D DEODORIZING FILTER

CROSS REFERENCE TO RELATED APPLICATIONS

This application is a National Stage of International Application No. PCT/KR2017/002680, filed on Mar. 13, 2017, which claims priority from Korean Patent Application No. 10-2016-0030229, filed on Mar. 14, 2016, the contents of all of which are incorporated herein by reference in their entirety.

TECHNICAL FIELD

The present invention relates generally to a 3D (three dimensional) deodorizing filter and, more particularly, to a 3D deodorizing filter allowing an airflow path to be formed in multiple directions thus enhancing airflow performance and improving deodorizing efficiency.

BACKGROUND ART

As well known in the art, a deodorizing filter is a filter that removes odor components in the air, and is formed by filling a core of the filter with a deodorizing agent such as activated carbon or zeolite, which has excellent ability to adsorb odor components.

A honeycomb-shaped grid frame is mainly used as the filter core. The deodorizing filter is structured such that the filter core is filled with the deodorizing agent, and the front and rear surfaces of the filter core are covered with a mesh net to prevent the deodorizing agent from separation.

The deodorizing filter causes air to flow from the front side to the rear side of the filter core, whereby the odor components are removed from the air flowing through the deodorizing agent filling the filter core.

In this case, since the airflow is formed in one direction from the front side to the rear side of the filter core, the path through which the odor components are removed while the air passes through the deodorizing agent is limited, which leads to a reduction in the deodorizing efficiency.

DISCLOSURE

Technical Problem

Accordingly, the present invention has been made keeping in mind the above problems occurring in the prior art, and an object of the present invention is to provide a 3D deodorizing filter allowing an airflow path to be formed in multiple directions, whereby airflow performance is enhanced, and pressure loss is reduced thus improving deodorizing performance.

Technical Solution

In order to accomplish the above object, the present invention provides a 3D deodorizing filter, including: a filter core formed by arranging a plurality of core blocks each having at least one chamber such that the filter core has a plurality of chambers; a deodorizing agent filling the respective chambers of the filter core; and a filter net attached to the filter core and supporting an arrangement of the core blocks, the filter net preventing the deodorizing agent filling the chambers from separation.

The chamber may be defined by partition walls of the core block, and an open hole is formed on each of left- and right-side partition walls defining left and right sides of the chamber, the open hole allowing airflow between the chambers of adjacent core blocks.

In detail, the core block may be formed in a rectangular shape having the at least one chamber defined by the partition walls at top, bottom, and the left and right sides thereof, and the chamber may be open at front and rear sides thereof to allow airflow to pass through the deodorizing agent filling the core block.

According to an embodiment of the present invention, the filter core may be formed in a flat panel shape by arranging the plurality of core blocks vertically and horizontally, and the plurality of chambers may be partitioned by the partition walls of the core blocks.

According to another embodiment of the present invention, the filter core may be formed in a zigzag panel shape by attaching a first filter net and a second filter net to front surfaces and rear surfaces of the core blocks arranged vertically and horizontally, respectively, such that the core blocks are connected to each other in a stacked manner by: cutting the first and second filter nets vertically at junctions between the core blocks arranged horizontally such that the first and second filter nets are cut in an alternate manner; and bending adjacent core blocks attached to uncut portions of the first and second filter nets at a predetermined angle.

According to a further embodiment of the present invention, the filter core may be formed in a cylindrical shape by: attaching a first filter net and a second filter net to front surfaces and rear surfaces of the core blocks arranged vertically and horizontally, respectively; cutting one of the first and second filter nets vertically at junctions between the core blocks arranged horizontally; and rounding the core blocks connected to each other by a remaining one of the first and second filter nets in one direction.

Further, a third filter net may be attached to each of the left- and right-side partition walls of the core block on which the open holes are formed, so that the arrangement of the core blocks arranged vertically and horizontally is supported and the deodorizing agent filling the chamber of the core block is prevented from separation.

Moreover, upper and lower holders may be coupled to upper and lower ends of the filter core filled with the deodorizing agent, respectively, thereby supporting the shape of the filter core.

Advantageous Effects

According to the 3D deodorizing filter of the present invention, airflow can be generated in various directions so that air can efficiently flow and the pressure loss due to airflow can be reduced, thereby improving the deodorizing performance. In addition, the path through which the odor components are removed while air passes through the deodorizing agent is increased, thereby increasing a time that air is in contact with the deodorizing agent thus improving the deodorizing efficiency.

BEST MODE

Hereinafter, embodiments of the present invention will be described in detail with reference to the accompanying drawings.

First Embodiment

Figure 1:
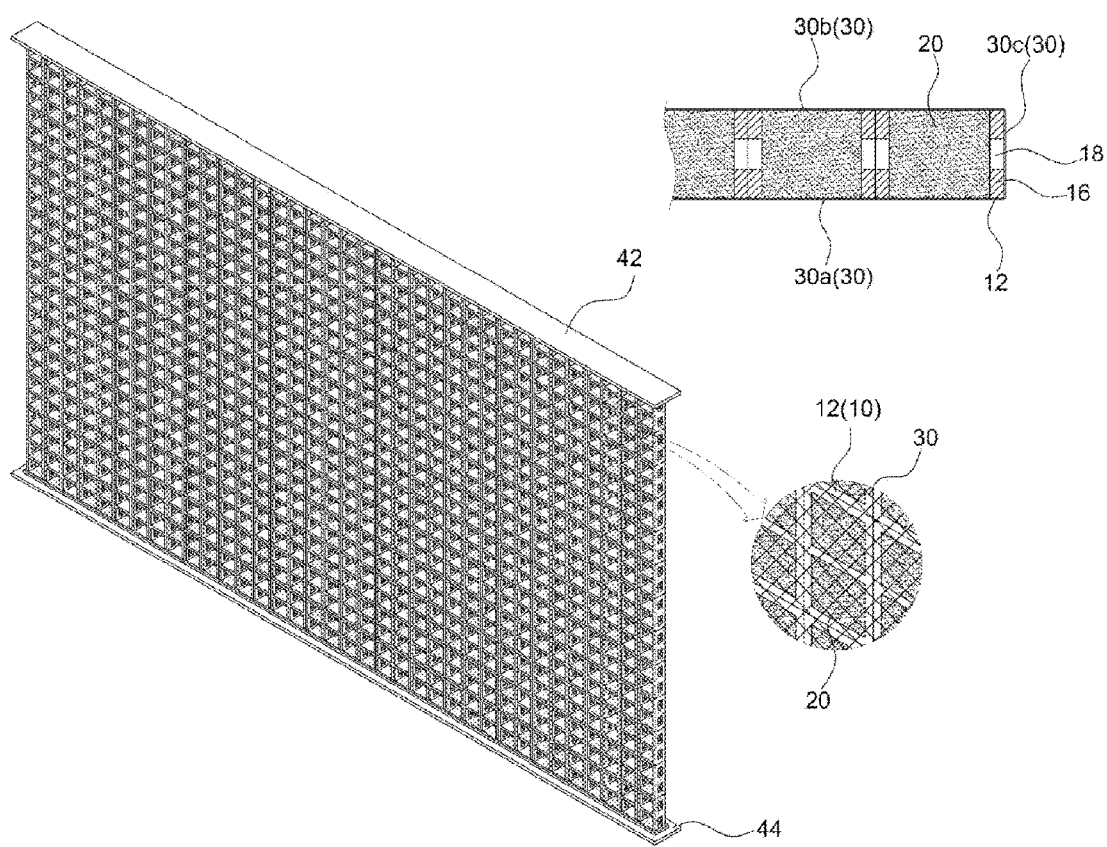
FIG. 1 is a view showing 1 a flat panel-type deodorizing filter according to an embodiment of the present invention.
Figure 2:
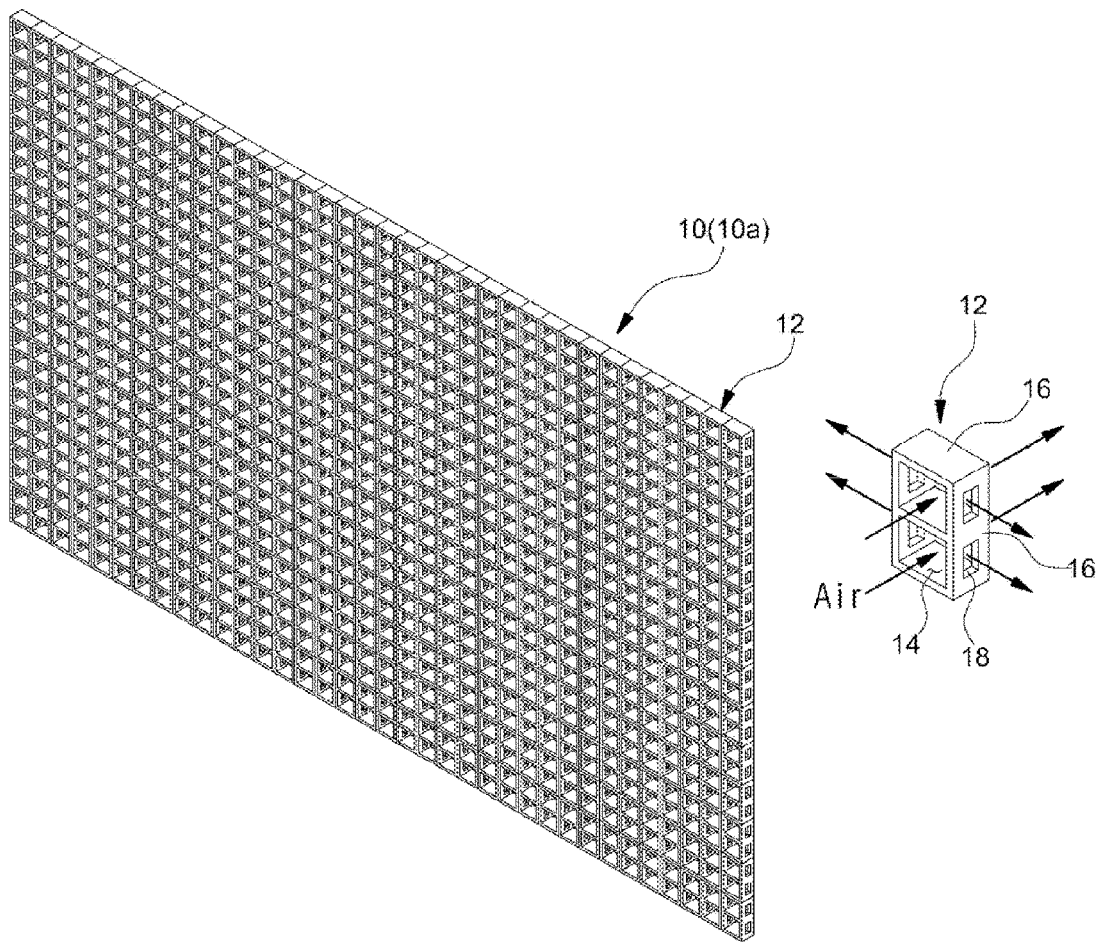
FIG. 2 is a perspective view showing a filter core of the flat panel-type deodorizing filter according to the embodiment of the present invention.

FIG. 1 shows a flat panel-type deodorizing filter according to an embodiment of the present invention, and FIG. 2 shows a filter core of the flat panel-type deodorizing filter while a filter net and the like remain omitted.

As shown in FIG. 1, the deodorizing filter according to the present invention includes a filter core 10, a deodorizing agent 20 filling the filter core 10, and a plurality of filter nets 30 attached to the surface of the filter core 10.

As shown in FIG. 2, the filter core 10 is formed by arranging a plurality of core blocks 12 each having at least one chamber filled with the deodorizing agent 20 such that the filter core has a plurality of chambers. The filter core is formed in a flat panel shape by arranging the plurality of core blocks 12 vertically and horizontally, and the plurality of chambers 14 are defined by partition walls 16 of the core blocks 12.

The core block 12 has a rectangular shape with at least one chamber 14. The chamber 14 is defined by the partition walls 16 at top, bottom, and left and right sides thereof, and an open hole 18 allowing airflow between the chambers 14 of adjacent core blocks 12 is formed on each of left- and right-side partition walls of the core block 12.

Explained more in detail, the core block 12 has a structure in which no open hole is formed on the upper and lower surfaces of the chamber 14 such that a deodorizing agent 20, e.g. particulate activated carbon, fills the chamber 14, and the open hole 18 is formed on each of the left- and right-side partition walls of the core block 12 such that airflow is allowed between the chambers 14 of the core blocks 12 being horizontally adjacent to each other. The chamber is open at front and rear surfaces thereof such that airflow passes through the core block 12 and the filter core 10.

Here, the open hole 18 may be formed in various sizes, numbers, and shapes such as a circle or a rectangle, and may be formed in a shape and a size corresponding to the left and right sides of the chamber 14. In the case that the open hole 18 is formed in a shape and a size corresponding to the left and right sides of the chamber 14, the left and right sides of the chamber 14 are open so that the left- and right-side partition walls defining the left and right sides of the chamber 14 are omitted.

In detail, the open hole 18 may be formed to have a size of a ratio of 70 to 98% of the surface area of each side of the chamber. When the surface area of the open hole 18 is less than 70% of the surface area of the each side of the chamber, air passing through the deodorizing agent 20 inside the chamber 14 may fail to efficiently flow, so that the deodorizing performance is deteriorated due to occurrence of pressure loss and a reduction in time air flows in the filter core 10a. When the surface area of the open hole 18 is greater than 98% of the surface area of the each side of the chamber 14, it is difficult to prevent the deodorizing agent 20 from separating from the chamber 14 due to the airflow.

Further, when the core block 12 has two or more chambers 14, the two or more chambers 14 are arranged in one direction (vertical direction or horizontal direction) such that adjacent chambers 14 are arranged with one partition wall interposed therebetween.

By arranging the core blocks 12 vertically and horizontally, it is possible to manufacture a flat panel-shaped filter core 10a having the plurality of chambers 14 arranged in a lattice form as shown in FIG. 2. Here, the core blocks 12 are arranged in a state in which the top, bottom, and left and side sides of the respective core blocks are in contact with each other, and the core blocks 12 are connected in a stacked manner by a first filter net 30a and a second filter net 30b that are attached to the front and rear surfaces of the core blocks 12 arranged in a flat arrangement, so that vertical and horizontal arrangement of the core blocks 12 are supported.

Although not shown in the drawing, in the case of the flat panel-shaped filter core 10a, the plurality of core blocks 12 are arranged vertically and horizontally in a fixed frame (not shown) so as not to move, and then the first filter net 30a is first attached to the front surfaces (or rear surfaces) of the arranged core blocks 12. Then, the deodorizing agent 20 fills the chamber 14 of each core block 12, and the second filter net 30b is attached to the rear surfaces (or the front surfaces) of the arranged core blocks 12.

Herein, the filter nets 30a and 30b are attached to the front and rear surfaces of the arranged core blocks 12, that is, front and rear surfaces of the filter core 10a are attached through hot fusion using a hot press. The filter nets 30a and 30b attached to the front and rear surfaces of the filter core 10a serve to prevent the deodorizing agent 20 filling the chambers 14 of the filter core 10a from separation, and serve to allow air to pass through the deodorizing agent 20. In addition, the filter nets serve to support the arrangement of the core blocks 12 arranged in the vertical and horizontal directions to ensure that the arrangement of the core blocks arranged vertically and horizontally is prevented from deformation.

Moreover, a filter net (third filter net 30c) is also attached to left sides of the outermost left core blocks 12 placed at the left end of the filter core 10a and right sides of the outermost right core blocks 12 placed at the right end of the filter core 10a. Accordingly, the deodorizing agent 20 filling the chambers 14 can be prevented from separation due to the open hole 18 of the core block 12.

In other words, the deodorizing agent 20, e.g. particulate activated carbon, capable of effectively adsorbing the odor components contained in the air fills the chambers 14 of the flat panel-shaped filter core 10a, and the filter nets 30a and 30b are attached to the front and rear surfaces of the filter core 10a so that the arrangement of the core blocks 12 can be supported without deformation.

Further, in order to support the arrangement of the core blocks 12 constituting the flat panel-shaped filter core 10a, that is, in order to support a predetermined shape (flat panel shape) of the filter core 10a according to the arrangement of the core blocks 12 to ensure that the predetermined shape of the filter core is prevented from deformation, an upper holder 42 and a lower holder 44 are coupled to upper and lower ends of the filter core 10a, respectively.

A first surface of each of the upper and lower holders 42 and 44 has a groove structure such that the filter core 10a can be supported by being inserted at the upper and lower ends thereof into the groove structure, while a second surface of each of the upper and lower holders has a flat plate structure so as to be mounted on the bottom or the like.

Referring to FIGS. 1 and 2, in the deodorizing filter employing the filter core 10a, air passing through the chambers 14 of the filter core 10a flows from the front side to the rear side of the filter core 10a, or from the rear side to the front side of the filter core 10a, and at the same time air flows in the left and right directions of the filter core 10a through the open holes 18 formed on the left and right sides of the core blocks 12. Accordingly, compared with the conventional filter core in which airflow is generated only in the front and rear directions, airflow can be generated in various directions so that air can efficiently flow and pressure loss due to airflow can be reduced, thereby improving deodorizing performance and reducing noises. In addition, the time that air flows in the filter core 10a is increased, thereby increasing the time that air is in contact with the deodorizing agent 20 thus improving deodorizing efficiency.

On the other hand, various types of deodorizing filters can be manufactured by arranging the core blocks 12 in a desired arrangement or by bending the filter core 10a into a desired shape.

Second Embodiment

Figure 3:
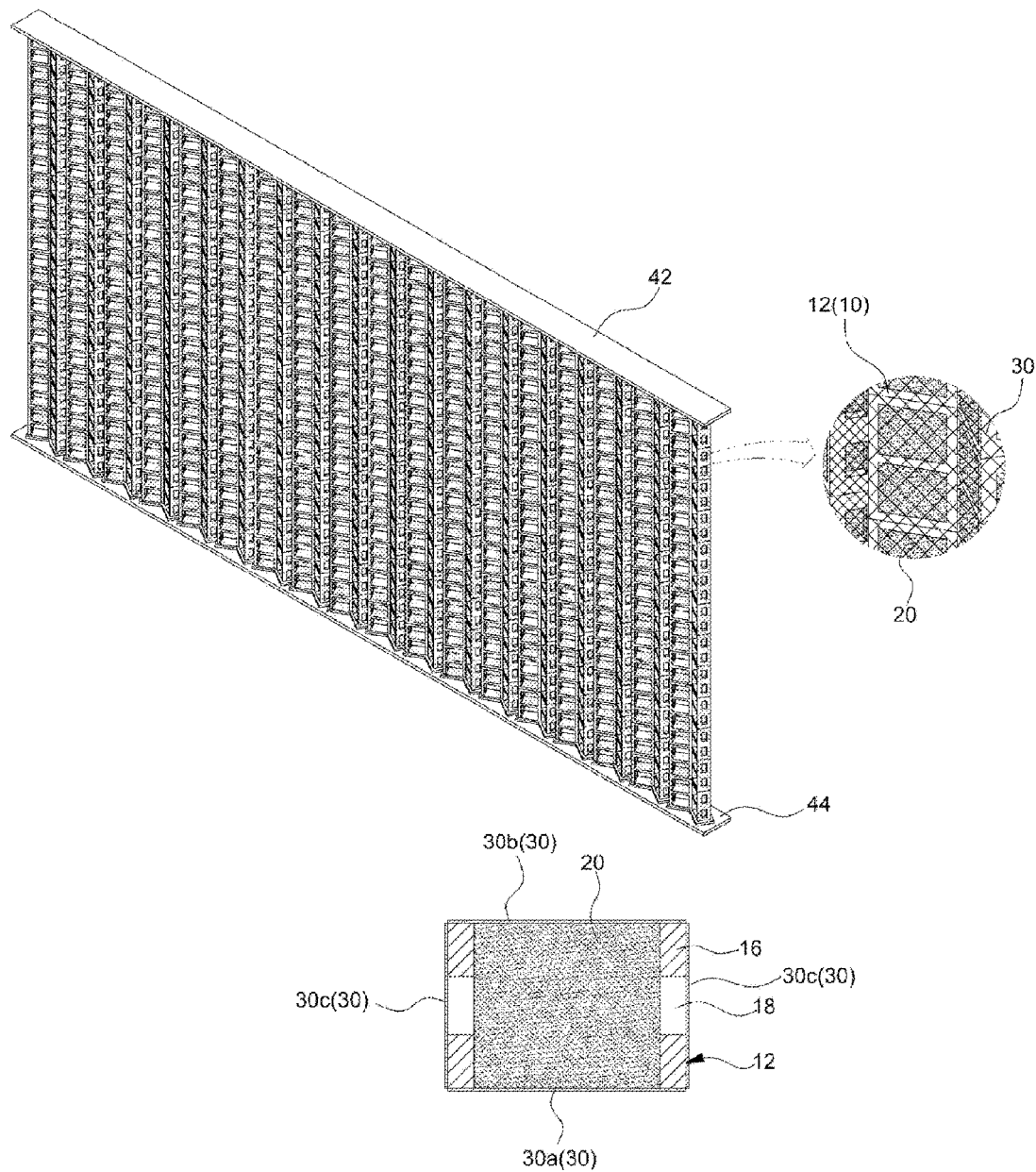
FIG. 3 is a view showing a zigzag panel-type deodorizing filter according to another embodiment of the present invention.
Figure 4A:
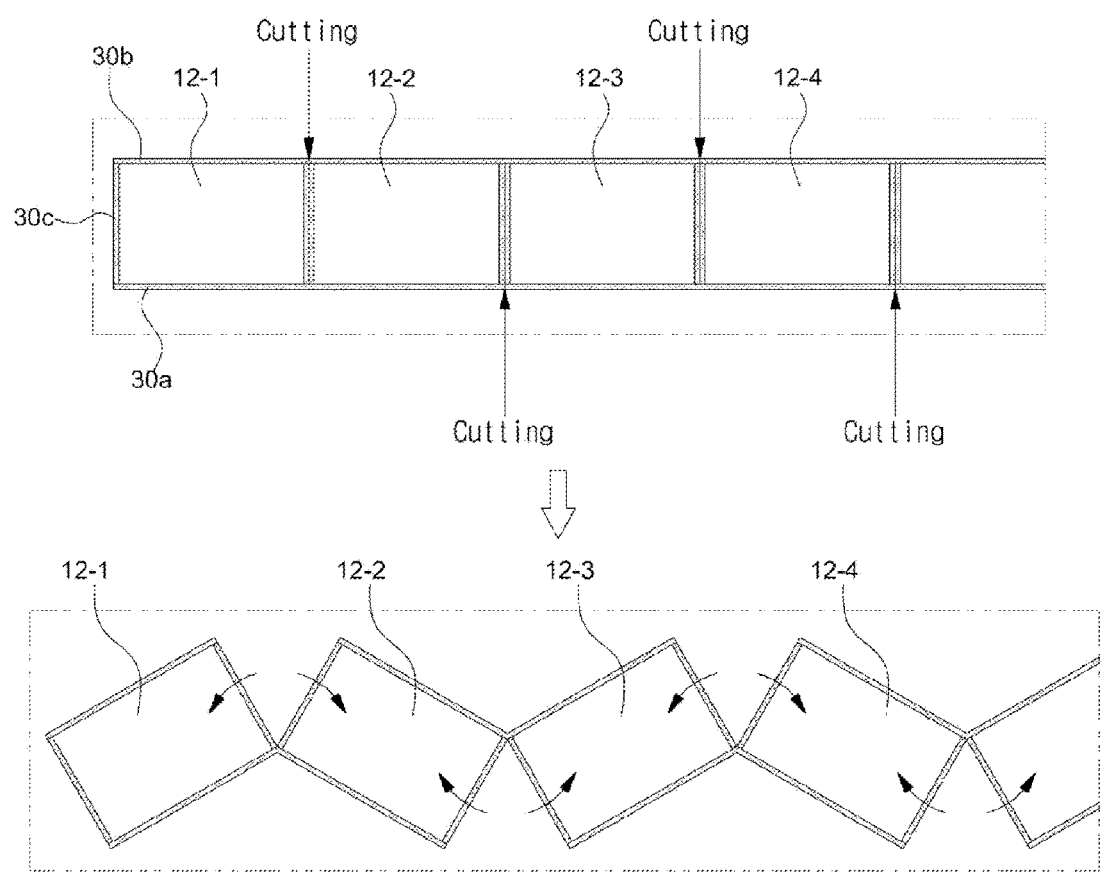
FIG. 4a is a plan view showing a manufacturing process of the zigzag panel-type deodorizing filter according to the another embodiment of the present invention.
Figure 4B:
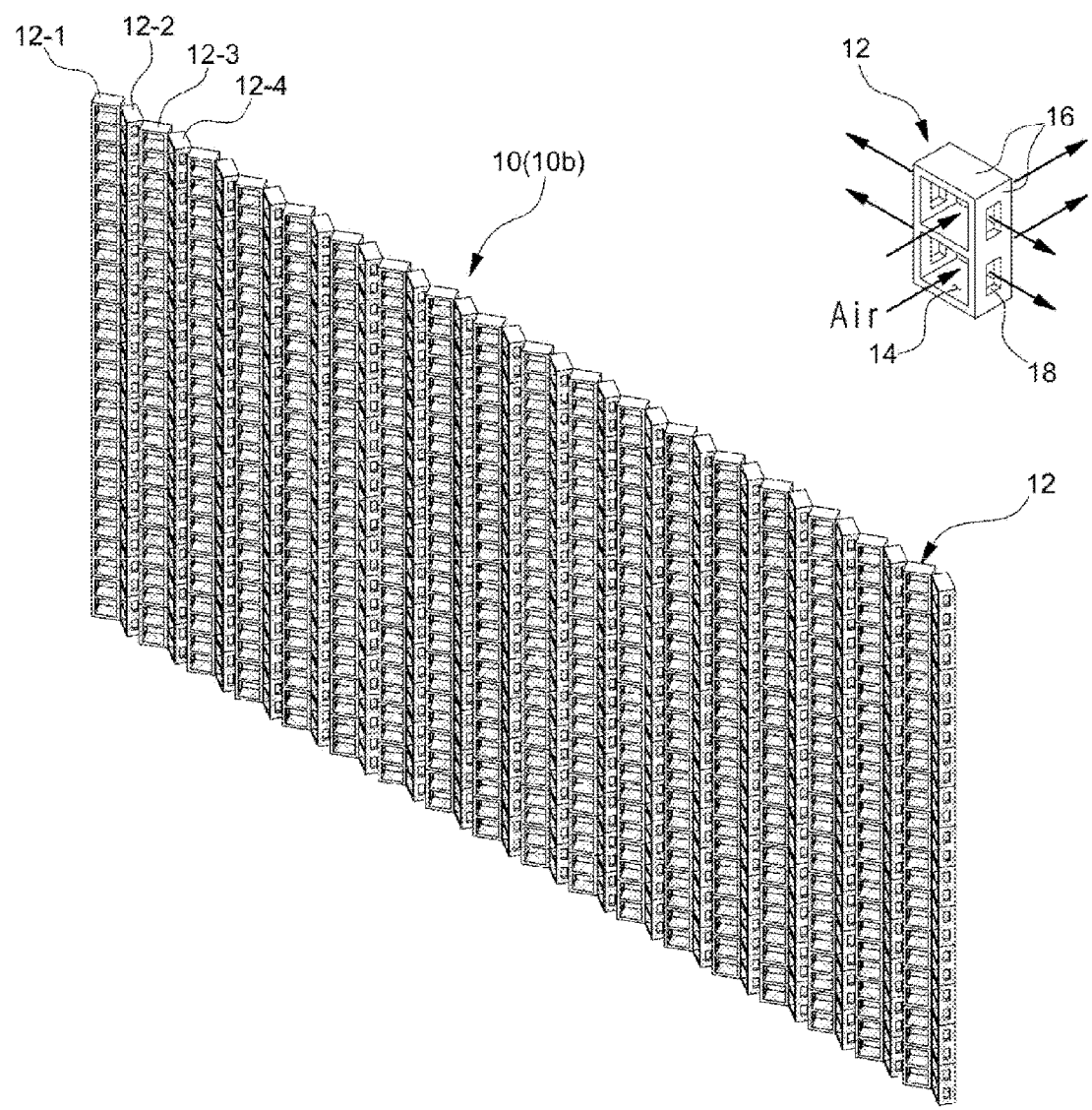
FIG. 4b is a perspective view showing a filter core of the zigzag panel-type deodorizing filter according to the another embodiment of the present invention.

FIG. 3 is a view showing a zigzag panel-type deodorizing filter according to another embodiment of the present invention, FIG. 4a is a plan view showing a manufacturing process of the zigzag panel-type deodorizing filter, and FIG. 4b is a view showing a filter core of the zigzag panel-type deodorizing filter while upper and lower holders are omitted.

It is possible to manufacture a zigzag panel-shaped filter core 10b as shown in FIGS. 3 and 4 by using the core block 12 having the structure described above in the first embodiment.

The filter core 10b is formed in a zigzag panel shape by arranging a plurality of core blocks 12 vertically and horizontally and then by alternately bending the horizontally arranged core blocks 12 forward and backward at a predetermined angle. The core blocks 12 are connected to each other in a stacked manner by a first filter net 30a and a second filter net 30b that are attached to front and rear surfaces of the core blocks 12 arranged vertically and horizontally, respectively, so that the arrangement of the core blocks 12 is supported. The first filter net 30a and the second filter net 30b are cut in the vertical direction at junctions between the core blocks 12 arranged horizontally in the flat arrangement such that the first and second filters 30a and 30b are cut in an alternate manner. Then, adjacent core blocks 12 attached to uncut portions of the first and second filter nets 30a and 30b are bent at a predetermined angle in a zigzag panel arrangement.

Referring to FIGS. 3 to 4b, for example, adjacent first and second core blocks 12-1 and 12-2 that are connected to each other by the first filter net 30a attached to the front surfaces of the core blocks are bent forward at a predetermined angle, and then a third core block 12-3 connected to the second core block 12-2 by the second filter net 30b attached to the rear surfaces of the core blocks is bent backward at a predetermined angle. Then, a fourth core block 12-4 connected to the third core block 12-3 by the first filter net 30a attached to the front surface of the core blocks is extended at a predetermined angle so as to be bent forward. After that, the above procedures are repeated, and thus the filter core 10b is formed in a zigzag panel shape having a W or M-shaped cross-sectional structure as viewed from above.

Explained more in detail, although not shown in the drawing, the present invention is not limited to cutting only one junction between the core blocks such as between the first and second core blocks or between the second and third core blocks as described above. Accordingly, when cutting a junction between the second and third core blocks connected by the first filter net 30a, a junction between the fourth and fifth core blocks connected by the second filter net 30b may be cut. Thus, the number of core blocks continuously connected in the zigzag panel arrangement may be changed depending on the situation.

Further, although not shown in the drawing, the core blocks 12 having the filter nets at the left and right sides thereof are arranged vertically and horizontally in a fixed frame (not shown) so as not to move, or the core blocks 12 arranged vertically are attached with the third filter net 30c to the left and right sides thereof and then arranged horizontally in the fixed frame (not shown) so as not to move. Then, the first filter net 30a is first attached to the front surfaces (or rear surfaces) of the core blocks 12 arranged vertically and horizontally in the fixed frame, whereafter the deodorizing agent 20 fills the chamber 14 of each core block 12.

Subsequently, the second filter net 30b is attached to the rear surfaces (or front surfaces) of the core blocks 12 arranged vertically and horizontally. Then, the first filter net 30a and the second filter net 30b are cut in the vertical direction at junctions between the horizontally arranged core blocks 12. Here, the first and second filter nets are cut alternately such that the first filter net 30a is cut at a junction between the core blocks 12, and then the second filter net 30b is cut at a junction between the core blocks 12. This alternating cutting procedure is repeated. Then, adjacent core blocks 12 attached to the uncut portions of the first filter net 30a and the second filter net 30b are bent at a predetermined inclination angle, thereby manufacturing a zigzag panel, a cabin type of filter core or corrugated filter core 10b.

Herein, by the filter nets 30a, 30b, and 30c that are attached to the open front and rear surfaces of the core blocks 12, and the left and right sides of the core blocks on which the open holes 18 are formed, the arrangement of the core blocks 12 arranged vertically and horizontally can be supported without deformation, and the deodorizing agent 20 can be prevented from separating from the chamber 14 of the core block 12.

Subsequently, the upper and lower ends of the filter core 10b are inserted into the upper holder 42 and the lower holder 44, so that the filter core 10b can be stably fixed in a zigzag panel shape.

Referring to FIGS. 3 and 4b, in the case of the deodorizing filter employing the zigzag panel-shaped filter core 10b, the air passing through the chambers 14 of the filter core 10b may flow from the front side to the rear side of the filter core 10b or from the rear side to the front side of the filter core 10b by passing through the chambers 14 in the forward and backward directions, and may simultaneously flow in the horizontal direction through the open holes 18 formed on the left and right sides of the core blocks 12.

Here, the open hole 18 may be formed in various sizes, numbers, and shapes such as a circle or a rectangle, and may be formed in a shape and a size corresponding to the left and right sides of the chamber 14. In the case that the open hole 18 is formed in a shape and a size corresponding to the left and right sides of the chamber 14, the left and right sides of the chamber 14 may be open so that the left- and right-side partition walls defining the left and right sides of the chamber 14 are omitted.

In detail, the open hole 18 may be formed to have a size of a ratio of 70 to 98% of the surface area of each side of the chamber. In the case that the open hole has the above size, as airflow is generated in various directions, air can efficiently flow and pressure loss due to airflow can be reduced, thereby improving deodorizing performance and reducing operation noises.

Third Embodiment

Figure 5:
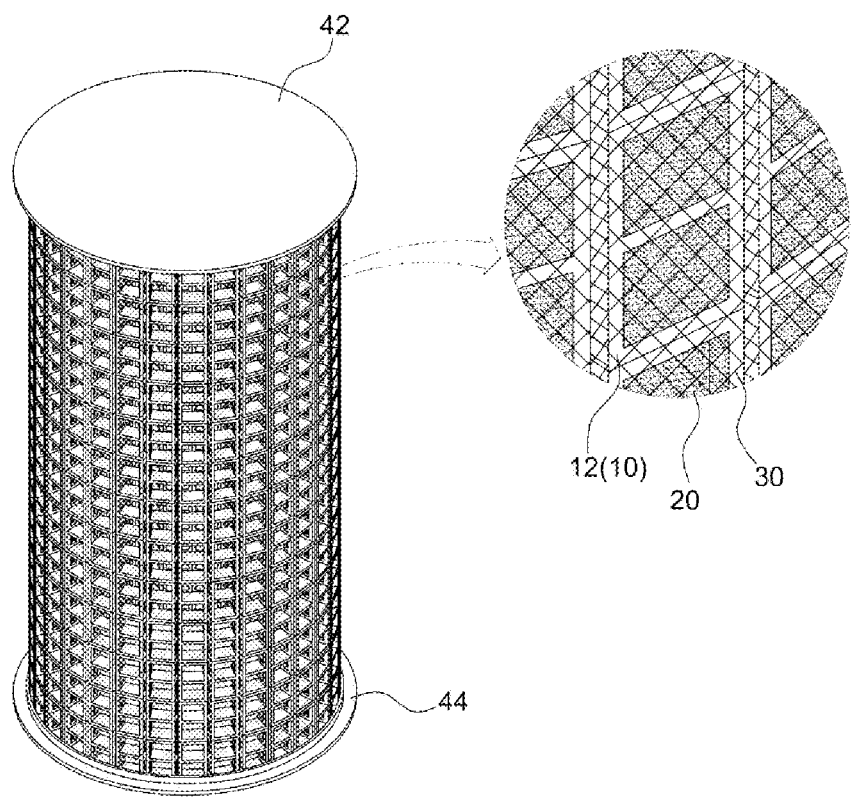
FIG. 5 is a perspective view showing a cylinder-type deodorizing filter according to a further embodiment of the present invention.
Figure 6A:
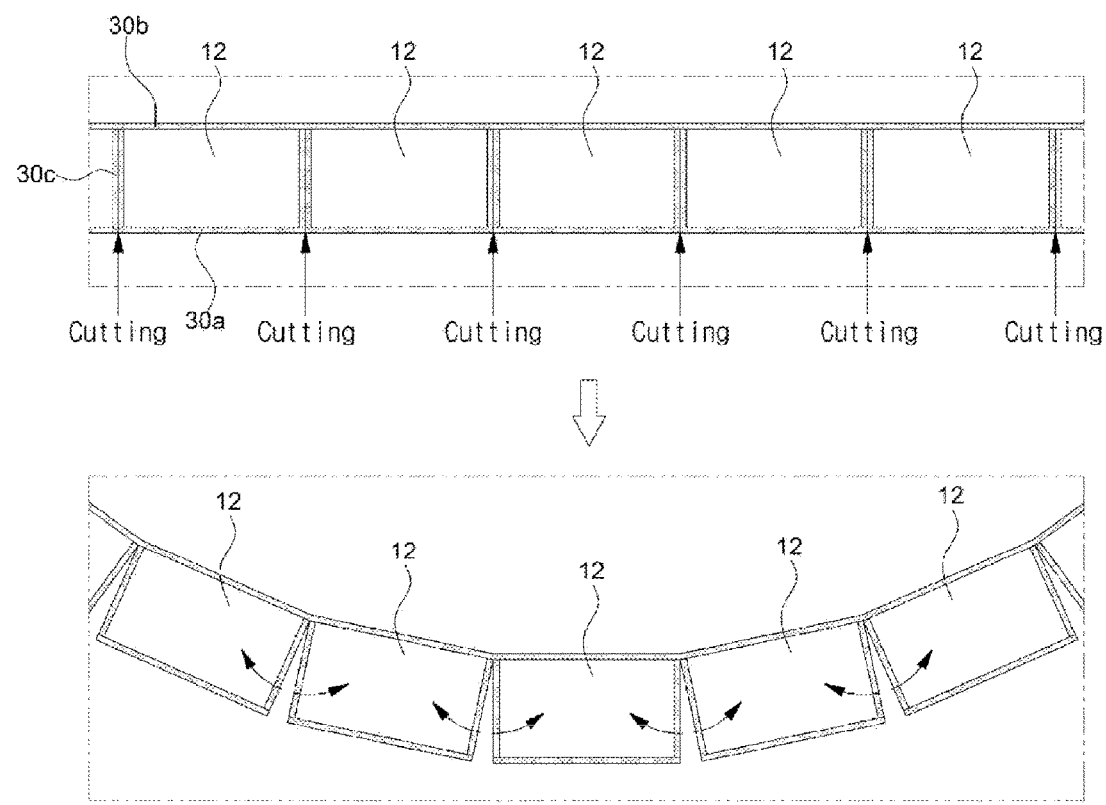
FIG. 6a is a plan view showing a manufacturing process of the cylinder-type deodorizing filter according to the further embodiment of the present invention.
Figure 6B:
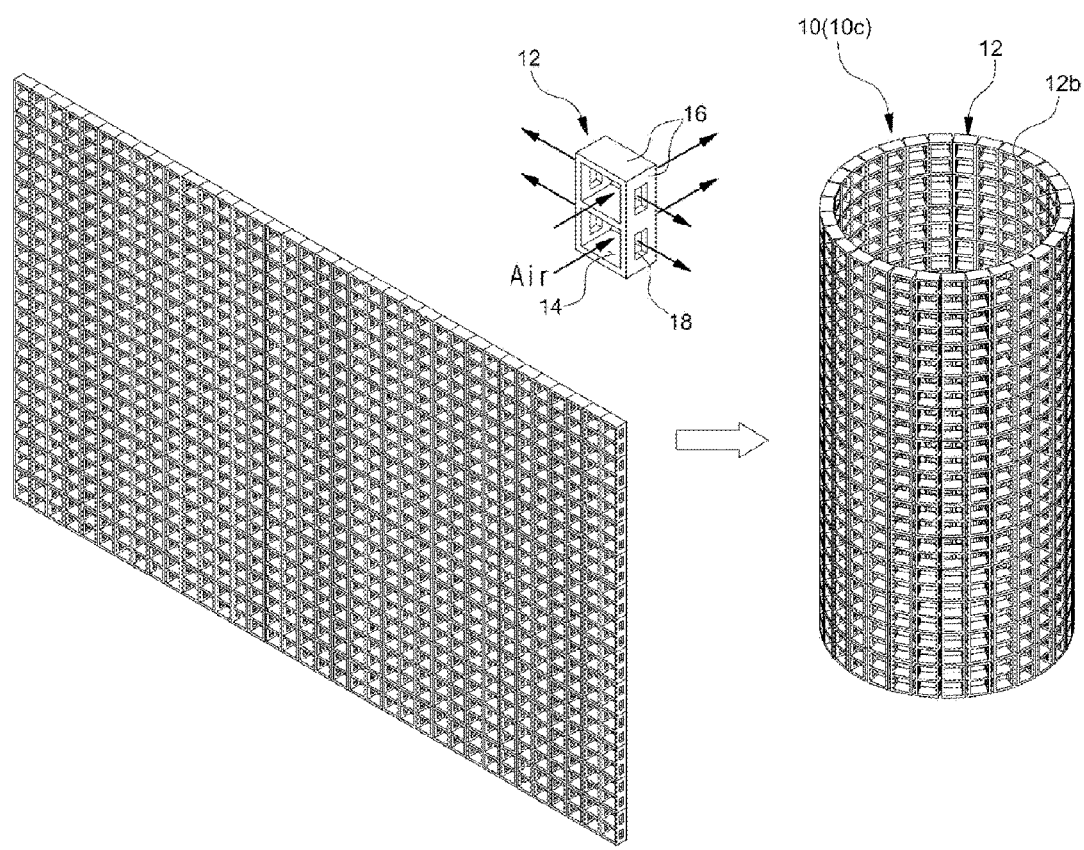
FIG. 6b is a perspective view showing a filter core of the cylinder-type deodorizing filter according to the further embodiment of the present invention.

FIG. 5 is a view showing a cylinder-type deodorizing filter according to a further embodiment of the present invention, FIG. 6A is a plan view showing a manufacturing process of the cylinder-type deodorizing filter, and FIG. 6b is a view showing a filter core of the cylinder-type deodorizing filter while a filter net and the like remain omitted.

It is also possible to manufacture a cylinder-shaped filter core 10c as shown in FIG. 5 by using the core block 12 having the structure above described in the first embodiment.

As shown in FIGS. 5 to 6b, the filter core 10c having a cylindrical shape is formed by arranging a plurality of core blocks 12 vertically and horizontally and then rounding the core blocks in one direction. The core blocks 12 are connected in a stacked manner by first and second filter nets 30a and 30b attached to front and rear surfaces of the core blocks 12 arranged vertically and horizontally, so that the vertical and horizontal arrangements of the core blocks 12 are supported without deformation. The first filter net 30a attached to the front surfaces of the core blocks 12 is cut in the vertical direction at all junctions between adjacent core blocks 12, and then the adjacent core blocks 12 connected by the uncut second filter net 30b attached to the rear surfaces of the core blocks are rounded in one direction in a cylindrical arrangement.

Explained more in detail, although not shown in the drawing, the core blocks 12 having the filter net at the left and right sides thereof are arranged vertically and horizontally in a fixed frame (not shown) so as not to move, or the core blocks are arranged vertically and then the core blocks 12 having the third filter net 30c at the left and right sides thereof are arranged horizontally in the fixed frame (not shown) so as not to move. Then, the first filter net 30a is first attached to the front surfaces (or rear surfaces) of the core blocks 12 arranged vertically and horizontally in the fixed frame, whereafter the deodorizing agent 20 fills the chamber 14 of each core block 12.

Next, the second filter net 30b is attached to the rear surfaces (or the front surfaces) of the core blocks arranged vertically and horizontally, and the first filter net 30a is cut in the vertical direction at all junctions between the adjacent core blocks 12. Then, the adjacent core blocks 12 connected by the second filter net 30b are rounded in one direction, thereby manufacturing the cylinder-shaped filter core 10c.

Herein, by the filter nets 30a, 30b, and 30c that are attached to the open front and rear surfaces of the core blocks 12, and the left and right sides of the core blocks on which the open holes 18 are formed, the arrangement of the core blocks 12 arranged vertically and horizontally can be supported without deformation, and the deodorizing agent 20 can be prevented from separating from the chamber 14 of the core block 12.

Subsequently, upper and lower ends of the filter core 10c are inserted into upper holder 42 and lower holder and fixed so as not to move or deform, so that the cylindrical shape of the filter core 10c can be stably maintained.

When the upper and lower ends of the filter core 10c are inserted into the upper and lower holders 42 and 44, the core blocks 12 placed at the left- and right-side ends (at the outermost sides) of the filter core 10c are in contact with each other at rear edge portions 12b or the left- and right-side ends of the second filter net 30b are in contact with each other.

In the deodorizing filter employing the cylinder-shaped filter core 10c, air passing through the chambers 14 of the filter core 10c may flow from the outside to the inside of the filter core 10c or from the inside to the outside of the filter core 10c, and may simultaneously flow in the horizontal direction through the open holes 18 formed on the left and right sides of the core blocks 12.

Here, the open hole 18 may be formed in various sizes, numbers, and shapes such as a circle or a rectangle, and may be formed in a shape and a size corresponding to the left and right sides of the chamber 14. In the case that the open hole 18 is formed in a shape and a size corresponding to the left and right sides of the chamber 14, the left and right sides of the chamber 14 may be open so that the left- and right-side partition walls defining the left and right sides of the chamber 14 are omitted.

In detail, the open hole 18 may be formed to have a size of a ratio of 70 to 98% of the surface area of each side of the chamber. In the case that the open hole has the above size, as airflow is generated in various directions, air can efficiently flow and pressure loss due to airflow can be reduced, thereby improving deodorizing performance and reducing operation noises.

Further, the above-described flat panel-shaped filter core 10a, the zigzag panel-shaped filter core 10b, and the cylinder-shaped filter core 10c may be integrally formed as a single injection molded product without using the core block 12. However, by assembling the above various types of filter cores 10 by using core block 12 allowing various airflow paths to be formed, only the injection mold for the core block 12 may be manufactured without preparing various injection molds according to the structure of the filter core 10. Thus, it is advantageous in that the mold production cost can be reduced.

Here, the core block 12 may be injection-molded by using a material such as polypropylene (pp).

MODE FOR INVENTION

Hereinafter, the present invention will be described in more detail with reference to experimental examples. These experimental examples of the present invention are presented to make complete disclosure of the present invention and help those who are ordinarily skilled in the art best understand the invention. Various changes to the following experimental examples are possible and the scope of the present invention is not limited to the following experimental examples.

The deodorizing performance, the pressure loss, and the energy efficiency of the flat panel-type, the zigzag panel-type, and the cylinder-type filter cores prepared by various experimental examples of the first to third embodiments, respectively, were measured by the following methods.

Experimental Example 1 (Examples 1-1 to 1-3 and Comparative Examples 1-1 to 1-2): Experiment on Area of Open Hole of Core Block in Flat Panel-Type Deodorizing Filter Examples 1-1 to 1-3 and Comparative Examples 1-1 to 1-2 were carried out according to the first embodiment described above, and as shown in Table 1 below, only the ratio (%) of the surface area of the open hole to the surface area of the each side of the chamber was varied and the properties were measured according to the following measuring method. The results are shown in Table 1 below. In detail, as shown in Table 1 below, the examples differ in the size of the open hole of the chamber of the core blocks thereof. The core blocks were arranged in a state in which the top, bottom, and left and right sides of the respective core blocks were in contact with each other, and then deodorizing agent filled the respective core blocks. After that, a flat panel-shaped filter core was prepared by attaching the first filter net to the front surfaces of the core blocks, the second filter net to the rear surfaces of the core blocks, and the third filter net to the left and right sides of the outermost left and right core blocks, thereby preparing, and then the upper and lower holders were assembled to the upper and lower ends of the filter core, respectively.

In the following Experimental Examples 2 and 3, the properties were measured by the same method as described below, and the results are shown in Tables 2 and 3 below.

(1) Deodorizing Performance

Deodorizing performance was evaluated by a clean air delivery rate (CADR) test of gaseous pollutants according to Chinese standard GB/T 18801-2015, and formaldehyde was used as the measurement gas.

For the experiment, air was circulated by operating a FAN provided inside a chamber, and an air cleaner equipped with an INTERSCAN Portable Analyzer (4000 Series) for measurement of Formaldehyde and filters of the Examples and Comparative Examples were set inside the chamber. Then, temperature (25±2)° C. and humidity (50±10)% inside the chamber were set, and 0.667 to 1 ppm or 0.8 to 1.2 mg/m3 of HCHO was injected by an HCHO Solution bubbling in a state where the FAN was turned on. After the HCHO was circulated and stabilized, the FAN was turned off and the HCHO was stabilized, and then the air cleaner was operated for 1 hour to measure the deodorizing performance.

(2) Pressure Loss

The filters of the Examples and Comparative Examples were mounted in a pressure loss measuring apparatus, and pressures (mmH$_2$O) at front and rear ends of the filter were measured at a line speed of 1 m/s, whereafter pressure loss was calculated by excluding the pressure at the rear end from the pressure at the front end.

(3) Energy Efficiency

The air cleaner equipped with the filters of the Examples and the Comparative Examples was connected to a power consumption meter (Korins Electronic Energy Meter, KEM2500), and the air cleaner was operated in a strong wind mode for 30 seconds to measure power consumption. Then, energy efficiency was calculated by dividing the previously measured deodorizing performance (CADR) by the measured power consumption.

TABLE 1

| | Ratio of Surface Area of Open hole to Surface Area of Each Side of Chamber (%) | Deodorizing Performance CADR(m3/h) | Pressure Loss (mmH2O) | Energy efficiency |
|---|---|---|---|---|
| Example 1-1 | 70 | 60 | 2.15 | 1.87 |
| Example 1-2 | 85 | 61 | 1.97 | 1.90 |
| Example 1-3 | 98 | 69 | 1.83 | 2.15 |
| Comparative Example 1-1 | 0 | 44 | 4.12 | 1.37 |
| Comparative Example 1-2 | 50 | 49 | 3.72 | 1.53 |

Experimental Example 2 (Examples 2-1 to 2-3 and Comparative Examples 2-1 to 2-2): Experiment on Area of Open Hole of Core Block in Zigzag Panel-Type Deodorizing Filter Examples 2-1 to 2-3 and Comparative Examples 2-1 to 2-2 were carried out according to the second embodiment described above, and as shown in Table 2 below, only the ratio (%) of the surface area of the open hole to the surface area of the each side of the chamber was varied and the properties were measured according to the following measuring method. The results are shown in Table 2 below. In detail, as shown in Table 2 below, the examples differ in the size of the open hole of the chamber of the core blocks thereof. The core blocks were arranged in a state in which the top, bottom, and left and right sides of the respective core blocks were in contact with each other, and then deodorizing agent filled the respective core blocks. After that, a filter core was prepared by attaching the first filter net to the front surfaces of the core blocks, the second filter net to the rear surfaces of the core blocks, and the third filter net to the left and right sides of the core blocks, and then the first filter net and the second filter net were cut in the vertical direction in an alternate manner at junctions between the adjacent core blocks. Then, the core blocks were alternately bent forward and backward at a predetermined angle to manufacture a zigzag panel-shaped filter core, and the upper and lower holders were assembled to the upper and lower ends of the filter core, respectively.

TABLE 2

| | Ratio of Surface Area of Open hole to Surface Area of Each Side of Chamber (%) | Deodorizing Performance CADR(m3/h) | Pressure Loss (mmH2O) | Energy efficiency |
|---|---|---|---|---|
| Example 2-1 | 70 | 121 | 1.73 | 3.27 |
| Example 2-2 | 85 | 126 | 1.67 | 3.40 |
| Example 2-3 | 98 | 119 | 1.45 | 3.21 |
| Comparative Example 2-1 | 0 | 74 | 3.95 | 2.05 |
| Comparative Example 2-2 | 50 | 75 | 3.53 | 2.02 |

Experimental Example 3 (Examples 3-1 to 3-3 and Comparative Examples 3-1 to 3-2): Experiment on Area of Core Block Open Hole in Cylinder-Type Deodorizing Filter Examples 3-1 to 3-3 and Comparative Examples 3-1 to 3-2 were carried out according to the third embodiment described above, and as shown in Table 3 below, only the ratio (%) of the surface area of the open hole to the surface area of the each side of the chamber was varied and the properties were measured according to the following measuring method. The results are shown in Table 3 below. In detail, as shown in Table 3 below, the examples differ in the size of the open hole of the chamber of the core blocks thereof. The core blocks were arranged in a state in which the top, bottom, and left and right sides of the respective core blocks were in contact with each other, and then deodorizing agent filled the respective core blocks. After that, a filter core was prepared by attaching the first filter net to the front surfaces of the core blocks, the second filter net to the rear surfaces of the core blocks, and the third filter net to the left and right sides of the core blocks, and then the first filter net was cut in the vertical direction at junctions between the adjacent core blocks. Then, the core blocks connected by the second filter net were rounded in one direction to manufacture a cylinder-type filter core, and the upper and lower holders were assembled to the upper and lower ends of the filter core, respectively.

TABLE 3

| | Ratio of Surface Area of Open hole to Surface Area of Each Side of Chamber (%) | Deodorizing Performance CADR(m3/h) | Pressure Loss (mmH2O) | Energy efficiency |
|---|---|---|---|---|
| Example 3-1 | 70 | 71 | 2.21 | 2.36 |
| Example 3-2 | 85 | 69 | 2.08 | 2.3 |
| Example 3-3 | 98 | 69 | 1.86 | 2.3 |
| Comparative Example 3-1 | 0 | 48 | 4.13 | 1.65 |
| Comparative Example 3-2 | 50 | 49 | 3.85 | 1.68 |

Referring to the physical property measurement results shown in Tables 1 to 3, when the surface area of the open hole is 70 to 98% of the surface area of the each side of the chamber, it can be confirmed that airflow passing through the deodorizing agent inside the chamber efficiently flows and thus the pressure loss is reduced. Further, the deodorizing performance is improved and the energy efficiency is also improved.

On the other hand, when the surface area of the open hole is equal to or less than 70% of the surface area of the each side of the chamber as in Comparative Examples 1-1 and 1-2, Comparative Examples 2-1 and 2-2, and Comparative Examples 3-1 and 3-2, it can be confirmed that the pressure loss is increased, and the deodorizing performance and energy efficiency are decreased as compared with Examples 1-1 to 1-3, Examples 2-1 to 2-3, and Examples 3-1 to 3-3. Consequently, in the case of the filter core including the core block in which the ratio of the surface area of the open hole to the surface area of the each side of the chamber is 70 to 98%, the deodorizing performance for removing the odor components, the pressure loss, and the energy efficiency are found to be advantageous as compared with the filter core including the core block in which the surface area of the open hole is equal to or less than 70% of the surface area of the each side of the chamber.

Although a preferred embodiment of the present invention has been described for illustrative purposes, those skilled in the art will appreciate that various modifications, additions and substitutions are possible, without departing from the scope and spirit of the invention as disclosed in the accompanying claims.

INDUSTRIAL APPLICABILITY

The present invention is applicable to a filter core for deodorizing agent filling and a deodorizing filter employing the same.

The invention claimed is:
1. A 3D deodorizing filter, comprising:
a filter core formed by arranging a plurality of core blocks each having at least one chamber, such that the filter core has a plurality of chambers;
a deodorizing agent filling the respective chambers of the filter core; and
a filter net attached to the filter core and supporting an arrangement of the core blocks, the filter net preventing the deodorizing agent filling the chambers from separation,
wherein the chamber is defined by partition walls of each core block, and an open hole is formed on each of left- and right-side partition walls defining left and right sides of the chamber, the open hole allowing airflow between the chambers of adjacent core blocks,
wherein the filter core is formed in a flat panel shape by arranging the plurality of core blocks vertically and horizontally and the plurality of chambers are partitioned by the partition walls of the core blocks,
wherein a third filter net is attached to each of the left- and right-side partition walls of the core block on which the open holes are formed.
2. The 3D deodorizing filter of claim 1, wherein the each core block is formed in a rectangular shape having the at least one chamber defined by the partition walls at top, bottom, and the left and right sides thereof, and the chamber is open at front and rear sides thereof to allow airflow to pass through the deodorizing agent filling the core block.
3. A 3D deodorizing filter, comprising:
a filter core formed by arranging a plurality of core blocks each having at least one chamber, such that the filter core has a plurality of chambers;
a deodorizing agent filling the respective chambers of the filter core; and
a filter net attached to the filter core and supporting an arrangement of the core blocks, the filter net preventing the deodorizing agent filling the chambers from separation,
wherein the chamber is defined by partition walls of each core block, and an open hole is formed on each of left- and right-side partition walls defining left and right sides of the chamber, the open hole allowing airflow between the chambers of adjacent core blocks,
wherein the filter core is formed in a zigzag panel shape by attaching a first filter net and a second filter net to front surfaces and rear surfaces of the core blocks arranged vertically and horizontally, respectively, such that the core blocks are connected to each other in a stacked manner by:

cutting the first and second filter nets vertically at junctions between the core blocks arranged horizontally such that the first and second filter nets are cut in an alternate manner; and bending adjacent core blocks attached to uncut portions of the first and second filter nets at a predetermined angle.

4. A 3D deodorizing filter, comprising:

a filter core formed by arranging a plurality of core blocks each having at least one chamber, such that the filter core has a plurality of chambers;

a deodorizing agent filling the respective chambers of the filter core; and a filter net attached to the filter core and supporting an arrangement of the core blocks, the filter net preventing the deodorizing agent filling the chambers from separation, wherein the chamber is defined by partition walls of each core block, and an open hole is formed on each of left- and right-side partition walls defining left and right sides of the chamber, the open hole allowing airflow between the chambers of adjacent core blocks, wherein the filter core is formed in a cylindrical shape by attaching a first filter net and a second filter net to front surfaces and rear surfaces of the core blocks arranged vertically and horizontally, respectively, by:

cutting one of the first and second filter nets vertically at junctions between the core blocks arranged horizontally; and rounding the core blocks connected to each other by a remaining one of the first and second filter nets in one direction.

5. The 3D deodorizing filter of claim 1, wherein upper and lower holders are coupled to upper and lower ends of the filter core filled with the deodorizing agent, respectively, thereby supporting the shape of the filter core.

6. The 3D deodorizing filter of claim 3, wherein a third filter net is attached to each of the left- and right-side partition walls of the core block on which the open holes are formed.

7. The 3D deodorizing filter of claim 4, wherein a third filter net is attached to each of the left- and right-side partition walls of the core block on which the open holes are formed.

8. The 3D deodorizing filter of claim 3, wherein upper and lower holders are coupled to upper and lower ends of the filter core filled with the deodorizing agent, respectively, thereby supporting the shape of the filter core.

9. The 3D deodorizing filter of claim 4, wherein upper and lower holders are coupled to upper and lower ends of the filter core filled with the deodorizing agent, respectively, thereby supporting the shape of the filter core.

10. The 3D deodorizing filter of claim 3, wherein the each core block is formed in a rectangular shape having the at least one chamber defined by the partition walls at top, bottom, and the left and right sides thereof, and the chamber is open at front and rear sides thereof to allow airflow to pass through the deodorizing agent filling the core block.

11. The 3D deodorizing filter of claim 4, wherein the each core block is formed in a rectangular shape having the at least one chamber defined by the partition walls at top, bottom, and the left and right sides thereof, and the chamber is open at front and rear sides thereof to allow airflow to pass through the deodorizing agent filling the core block.

* * * * *